US008551312B2

(12) United States Patent
Heus et al.

(10) Patent No.: US 8,551,312 B2
(45) Date of Patent: Oct. 8, 2013

(54) PROCESS TO PREPARE AMINO ACID-N, N-DIACETIC ACID COMPOUNDS

(75) Inventors: Martin Heus, Arnhem (NL); Hans Lammers, Arnhem (NL); Arie Volmer, Gulpen (NL)

(73) Assignee: Akzo Nobel N.V., Arnhem (NL)

( * ) Notice: Subject to any disclaimer, the term of this patent is extended or adjusted under 35 U.S.C. 154(b) by 469 days.

(21) Appl. No.: 12/516,911

(22) PCT Filed: Nov. 27, 2007

(86) PCT No.: PCT/EP2007/062881
§ 371 (c)(1),
(2), (4) Date: May 29, 2009

(87) PCT Pub. No.: WO2008/065109
PCT Pub. Date: Jun. 5, 2008

(65) Prior Publication Data
US 2010/0126864 A1    May 27, 2010

Related U.S. Application Data

(60) Provisional application No. 60/872,465, filed on Nov. 30, 2006.

(30) Foreign Application Priority Data

Mar. 15, 2007   (EP) .................................. 07104264

(51) Int. Cl.
*B01D 61/42*  (2006.01)
(52) U.S. Cl.
USPC .......................................... 204/541; 204/544
(58) Field of Classification Search
USPC .................................. 204/541, 544; 205/435
See application file for complete search history.

(56) References Cited

U.S. PATENT DOCUMENTS 6,334,944 B1 *  1/2002  Nambu et al. ................. 205/435

FOREIGN PATENT DOCUMENTS

| EP | 1 004 571 | 5/2000 |
| JP | 2001-226335 A | 8/2001 |
| WO | WO 2005/014527 | 2/2005 |

OTHER PUBLICATIONS

International Search Report and Written Opinion, International PCT Application No. PCT/EP2007/062881, mailed Mar. 13, 2008.

(Continued)

*Primary Examiner* — Arun S Phasge
(74) *Attorney, Agent, or Firm* — Timothy D. Meade

(57) ABSTRACT

The invention relates to a process for the production of an amino acid having at least one secondary or tertiary amino group and three or more carboxyl groups or its salt with less than an equivalent of alkaline metal based on the number of carboxyl groups, said process comprising reducing alkali metal ions from an aqueous solution of an alkali metal salt of an amino acid having at least one secondary or tertiary amino group and three or more carboxyl groups and acidifying the amino carboxylate starting material by first performing a chemical acidification step using an organic or inorganic acid to get a compound in which at least one of the groups is protonated, and in a subsequent step further acidifying the amino carboxylate starting material and reducing alkali metal ions from an aqueous solution of the partially acidified alkali metal salt of the amino acid having at least one secondary or tertiary amino group and three or more carboxyl groups by electrodialysis, wherein the electrodialysis is performed using a hydrogen ion permselective membrane on the anode side and a cation-permeable membrane on the cathode side.

15 Claims, 1 Drawing Sheet

(56) References Cited

OTHER PUBLICATIONS

International Preliminary Report on Patentability, International PCT Application No. PCT/EP2007/062881, mailed Mar. 2, 2009.
European Search Report, European Application No. EP 07 10 4264, dated Sep. 18, 2007.
Office Action dated Nov. 27, 2012 from corresponding Japanese Patent Application No. 2009-538696.
English Abstract for JP 2001-226335 A dated Aug. 21, 2001.

* cited by examiner

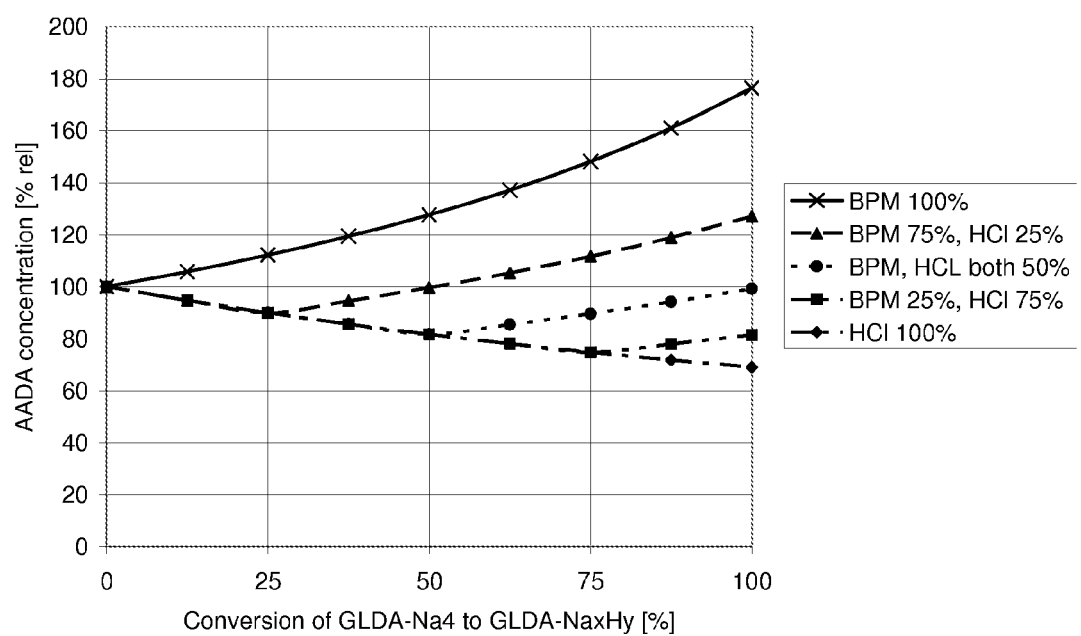

PROCESS TO PREPARE AMINO ACID-N, N-DIACETIC ACID COMPOUNDS

REFERENCE TO RELATED APPLICATION(S)

This application is the U.S. National Phase of PCT/EP2007/062881 filed on Nov. 27, 2007 and claims the benefit of U.S. Provisional Application No. 60/872,465 filed on Nov. 30, 2006.

The present invention relates to an improved process for reducing alkali metal ions from an aqueous solution of an alkali metal salt of an amino acid having at least one secondary or tertiary amino group and three or more carboxyl groups (hereinafter referred to as "AADA"). More specifically, it relates to a production process for an aqueous solution of an acid form of AADA in high yield by reducing alkali metal ions from an aqueous solution of an AADA alkali metal salt.

EP 1004571 discloses a production process for an amino acid having a secondary or tertiary amino group and three or more carboxyl groups, which contains reduced or no alkali metal ion and is high in biodegradability. The process encompasses reducing alkali metal ions from an aqueous solution of an alkali metal salt of an AADA by electrodialysis. The electrodialysis may be performed using a hydrogen ion permselective membrane on the anode side and a cation permeable membrane on the cathode side. This production process has the disadvantage that the solution entering the electrodialysis unit is corrosive, has a high viscosity, and the process is very energy-consuming. It is specifically indicated in EP 1004571 that a concentration of the AADA alkali metal salt above 60% is not possible, as the viscosity then becomes so high that the diffusibility of the solution deteriorates and the dialysis efficiency per hour decreases.

It is generally known that to suitably perform a BPM electrodialysis process the samples to be electrodialyzed preferably should have not too high viscosity (preferably, it is said to be below 15 cPoise at 40° C.) to prevent a too low flow. Though this too low flow can sometimes be partially compensated by a high pressure, which is energy consuming, a too low flow frequently results in a concentration polarization, leading to an uneven current distribution with the risk of the membranes of the electrodialysis cell being burnt or at least of a significant deterioration of the membranes.

The purpose of the present invention is to provide an improved process to prepare an amino acid having at least one secondary or tertiary amino group and three or more carboxyl groups, which contains reduced or no alkali metal ion, in which no highly corrosive materials and high viscous materials need to be electrodialytically acidified, while at the same time highly concentrated solutions can be prepared, and which provides a better balance between the use of energy and chemicals, additionally leading to a good balance between adding water and removing water from the reaction system, which process specifically uses less energy than the state of the art process when recalculating the use of chemicals into equivalent energy use.

The invention provides a process for the production of an amino acid having at least one secondary or tertiary amino group and three or more carboxyl groups or its salt with less than an equivalent of alkaline metal based on the number of carboxyl groups, said process comprising reducing alkali metal ions from an aqueous solution of an alkali metal salt of an amino acid having at least one secondary or tertiary amino group and three or more carboxyl groups and acidifying the amino carboxylate starting material by first performing a chemical acidification step using an organic or inorganic acid to get a compound in which at least one of the groups is protonated, and in a subsequent step further acidifying the amino carboxylate starting material and reducing alkali metal ions from an aqueous solution of the partially acidified alkali metal salt of the amino acid having at least one secondary or tertiary amino group and three or more carboxyl groups by electrodialysis, wherein the electrodialysis is performed using a hydrogen ion permselective membrane on the anode side and a cation permeable membrane on the cathode side.

As indicated above, the chemical acidification step will be continued until at least one of the groups of the amino acid starting material is protonated. In the net chemical reaction the first group to be protonated is said to be one of the carboxylate groups, which is then indicated as being converted to a carboxylic acid group; however, in a number of the amino acids covered by the present invention actually (one of) the amino group(s) is first protonated (resulting in an ammonium carboxylate), as the group having the highest pKa in the molecule is an amino group and not a carboxylate group. Therefore, the term "at least one of the groups" means the group of amino acid starting material having the highest pKa.

Chemical acidification takes away the necessity to use a lot of energy (electricity) for the part of the acidification that can quite conveniently be achieved by reaction with a (common) acid. $H^+$ generation by electrodialysis of water is never 100% efficient when operating a bipolar membrane electrodialysis cell. In general, current efficiency is in the order of 65-75%, which is directly related to the efficiency of $H^+$ generation. When using acids where the pH is sufficiently lower than the pH of the AADA to be acidified, substantially all $H^+$ is used, resulting in a higher efficiency, even up to and including 100% when expressed in $H^+$ consumption by the AADA. A sufficiently lower pH in the context of this application means at least 1 lower, preferably at least 1.5 lower. In consequence, when comparing the use of chemicals and electricity for acidification of an AADA, it was been found that when using chemical acidification, this can be recalculated to cost significantly less energy than electrolytical acidification.

On the other hand, the advantages of BPM electrodialysis, namely that crystallization-separation of the crystals of an AADA salt (where the crystals are formed by e.g. anti-solvent crystallization conducted by the addition of an organic solvent) is not needed, and the efficient reduction of alkali metal ions from the aqueous solution of an AADA alkali metal salt, especially for the part of the reduction where a stronger acid would be required, are maintained. In essence, as already indicated before, BPM electrodialysis can in addition be a waste-free process to produce completely acidified AADAs (i.e. no inorganic salt formation) if the alkaline solution formed during the process is (re)used. Further advantages of the process according to the invention are that the inlet stream to the electrodialyzer is much less corrosive and has a significantly lower viscosity than the non-acidified AADA, i.e. the AADA where all carboxylic acid groups are in their alkali metal salt form. In the process according to the invention, the size of the BPM unit can be decreased compared to the state of the art process disclosed in EP 1004571.

Additionally, when using the process of the present invention, a good balance is acquired between adding and removing water from the reaction system while at the same time keeping the salt load in the end product under control. The reduction of cations, such as alkali metal ions, in a bipolar membrane electrodialysis acidification results in the withdrawal of water from the reaction system due to osmotic forces. In a chemical acidification, on the other hand, water is suitably added to the system. Combining these two acidification steps in one process gives an aqueous AADA product in a system that is not so diluted that evaporating water is needed to obtain a reasonably concentrated product nor so concentrated that one will run into problems related to handling concentrated AADA solutions, like undesired crystallization of the AADA, and extremely high viscosity or corrosivity.

It should be noted that in EP 1004571 a process is disclosed which comprises adding an inorganic or an organic acid to the aqueous solution of an alkali metal salt of an AADA to give an alkali metal salt of an inorganic or an organic acid, and subsequently electrodialyzing the resultant solution with an anion-permeable membrane on the anion side and a cation-permeable membrane on the cathode side in order to remove the inorganic salt or the organic salt formed by the addition of the mentioned (in)organic acid.

Bipolar membrane electrodialysis (BPM), which is basically the same as electrodialysis using a hydrogen ion permselective membrane, is the most advantageous electrodialysis process This is because when using other electrodialysis methods than BPM electrodialysis—i.e. those based on the use of anion- and cation-permeable membranes only—the byproduct normally is a salt, which is to be considered a waste stream. In a BPM electrodialysis process it is possible to produce an alkaline solution as a byproduct, which is a side stream that is of value, for example because it can be used in the preparation of the AADA starting compound. A drawback to using anion exchange membranes in this application is the potential loss of AADA anions present in the process, because these anions can also migrate through the anion-permeable membranes as a result of the forces of the potential difference, causing a loss of valuable AADA product and polluting the aqueous alkali metal hydroxide by-product.

The alkali metal salt of the amino acid-N,N-diacetic acid preferably is a salt represented by the following formula (1)

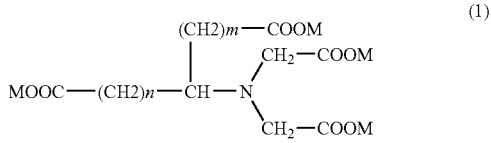

or formula (2)

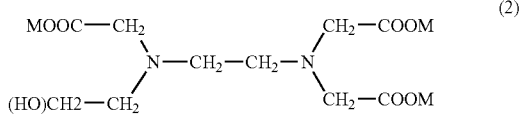

wherein M represents an alkali metal, m represents 0 or an integer of from 1 to 2, and n represents 0 or an integer of from 1 to 3.

As examples of alkali metal salts of amino acid-N,N-diacetic acid may be mentioned alkali metal salts of glutamic acid-N,N-diacetic acid (GLDA), alkali metal salts of aspartic acid-N,N-diacetic acid, alkali metal salts of glycine-N,N-diacetic acid, alkali metal salts of alpha-alanine-N,N-diacetic acid, alkali metal salts of beta-alanine-N, N-diacetic acid, of hydroxyethyl ethylenediamine triacetic acid (HEDTA), methylglycine diacetic acid (MGDA), and alkali metal salts of serine-N,N-diacetic acid.

In one embodiment the amino acid-N,N-diacetic acid—when fully acidified—has a solubility of at least about 1 gram per 100 grams of water. Preferably, the amino acid-N,N-diacetic acid has a solubility of at least about 5 grams per 100 grams of water. More preferably, it has a solubility of at least about 10 grams per 100 grams of water.

In a preferred embodiment it is an alkali metal salt of hydroxyethyl ethylenediamine triacetic acid (HEDTA), methylglycine diacetic acid (MGDA) or glutamic acid diacetic acid (GLDA). Particularly preferably, it is an alkali metal salt of glutamic acid-N,N-diacetic acid.

FIG. 1 is a schematic view of an electrodialyzer that can be used in the invention.

An electrodialysis process utilizes the principle that when positive and negative electrodes are put in an aqueous solution of an electrode solution and an electric potential gradient is applied thereto, positive and negative ions in the solution will move toward their respective counterelectrodes, and this means a treatment of arranging an ion exchange membrane and a semipermeable membrane between the two electrodes and carrying the two types of ions in the solution between the membranes in different directions to eliminate the ions from the membranes.

In the electrodialysis process, the electrodialysis is performed with a hydrogen ion permselective membrane on the anode side and a cation-permeable membrane on the cathode side. According to the electrodialysis to be used in the production process as shown in FIG. 1, each membrane cell through which an aqueous solution of an AADA alkali metal salt (referred to as "sample" S in the figure) passes comprises a hydrogen ion permselective membrane H as a semipermeable membrane on the anode side and a cation-permeable membrane C as an ion exchange membrane on the cathode side. An aqueous solution A is fed on the (other) side of the hydrogen ion permselective membrane H and the cation-permeable membrane C, respectively. In this procedure, alkali metal ions in the aqueous solution of an AADA alkali metal salt move toward a counterelectrode, i.e. toward the cathode, and permeate through the membrane C and migrate into the aqueous solution A, because the permeable membrane on the cathode side is the cation-permeable membrane C. In effect, hydrogen ions migrate separately from the aqueous solution on the anode side through the hydrogen ion permselective membrane H to the aqueous solution of AADA alkali metal salt. By this mechanism, alkali metal ions in the aqueous solution of AADA salt are replaced with hydrogen ions to reduce the number of alkali metal ions in the aqueous solution of AADA salt.

The term "hydrogen ion permselective membrane" as used herein means a functional membrane through which only hydrogen ions are permeable and other cations or anions are impermeable, and which is a hybrid membrane composed of laminated cation exchange membrane and anion exchange membrane. When an electric potential gradient is applied to the membrane, water is decomposed to form hydrogen ions and hydroxide ions, and the hydrogen ions and hydroxide ions move toward the cathode side and the anode side, respectively, and the hydroxide ions react with hydrogen ions in the aqueous solution A to form water or to make the aqueous solution (more) alkaline. Thus, only hydrogen ions can apparently permeate through the membrane. As examples of commercially available hydrogen ion permselective membranes may be mentioned Selemion HSV (manufactured by Asahi Glass Co., Ltd.) and NEOSEPTA BP1 (manufactured by Tokuyama Corporation).

The term "cation permeable membrane" means a functional membrane through which cations are permeable and anions are impermeable. For the membrane, use can advantageously be made of a membrane which at high densities retains a sulfonic acid group, a carboxylic acid group, and other groups which will have a negative charge when dissociated, and which is composed of a styrenic polymeric homogenous membrane. Commercially available membranes include, for instance, Selemion CMV (manufactured by Asahi Glass Co., Ltd.), Aciplex CK-1, CK-2, K-101, and K-102 (manufactured by Asahi Chemical Industry Co., Ltd.), Neosepta CL-25T, CH-45T, C66-5T, and CHS-45T (manufactured by Tokuyama Corporation), and Nafion 120, 315, and 415 (manufactured by Du Pont Company). The membrane can be chosen according to the species of alkali metal salt of amino acid diacetic acid or impurities to be removed.

The acids that can be used in the first step of the process include any and all acids, including solutions thereof in for example water, that are strong enough to at least fully protonate one of the (carboxylate) groups of the starting material. As the acid to be used in the first step may be mentioned, for instance, aqueous solutions of sulfuric acid, hydrochloric acid, phosphoric acid, nitric acid, and other inorganic acids, formic acid, acetic acid, propionic acid, glycolic acid, oxalic acid, and citric acid. The amount of the acid can be calculated based upon the amount of alkali metal ions to be removed.

Preferred organic acids are those organic acids of which the anions remaining after proton delivery to the AADA salt do not undesirably increase the tendency of the AADA end product to crystallize or precipitate. Also, the organic salt that is formed after adding the organic acid to the AADA salt preferably should neither crystallize nor precipitate. Also preferred are organic acids where the pKa is such that they are not readily protonated by the BPM electrodialytic acidification. This is generally the case when the pH of the mixture after treatment in the BPM unit is higher than this pKa, suitably it is at least 1.0 higher, preferably it is at least 1.5 higher. Examples of preferred organic acids to be used in the production process are formic acid, acetic acid, and other low molecular weight, cheap and relatively acidic organic acids, including aqueous solutions thereof. Preferred inorganic acids to be used for the acidification include inorganic acids like hydrochloric acid, hydrobromic acid, sulfuric acid, phosphoric acid, and nitric acid, including aqueous solutions thereof. Other acids suitable for the first step of the process are amino acid-N,N-diacetic acid compounds where a substantial part or all of the carboxylate groups are converted to carboxylic acid groups and proton exchange resins. In a preferred embodiment the chemical acidification of the first step of the process is performed using an amino acid having at least one secondary or tertiary amino group and three or more carboxyl groups or its salt with less than an equivalent of alkaline metal based on the number of carboxyl groups produced in the subsequent electrodialysis as the acid. In this embodiment, AADA salt is (continuously) added to already (partially) acidified AADA resulting from the process of the invention and the acquired process mixture is subsequently subjected to the electrodialysis step of the invention.

The use of inorganic acids, like hydrogen chloride, hydrogen bromide, sulfuric acid, and nitric acid, in addition to their being cheap and available in high molarity aqueous solutions has the additional advantage that the anions thereof, such as the chloride anions, give the aqueous solution subjected to electrodialysis an improved conductivity, while the anion itself does not have a detrimental effect on either the process or the resulting end product.

The use of the acid form of the amino acid-N,N-diacetic acids itself has as an additional beneficial effect that an AADA end product is provided in which no anion impurity is present.

As indicated above, ion (proton) exchange resins can also be suitably used as the acid for the first step of the process. They have an excellent acidity and are easy to separate from the other reactants. The major part of the ion exchange resins sufficiently acidic to be able to acidify an alkali metal salt of an amino acid-N,N-diacetic acid are characterized by the fact that they have a relatively low capacity. This low capacity does not make the resins unsuitable for the process according to this invention, as they need only be capable of providing a partial chemical acidification of the AADAs.

The concentration of the aqueous solution of an AADA alkali metal salt should preferably fall in the range from 5 to 70 wt %. The concentration more preferably is 10 wt % or more, and typically preferably 20 wt % or more, and more preferably 60 wt % or less, and typically preferably 50 wt % or less.

A concentration of the aqueous solution of AADA alkali metal salt of less than 5 wt % will cause deterioration of the productivity and may require concentration operation after dialysis, and is impractical.

In this connection, when the produced AADA is glutamic acid-N,N-diacetic acid, methylglycine N,N-diacetic acid, hydroxyethylethylenediamine triacetic acid or serine diacetic acid, the aqueous solution of the AADA salt can be treated in high concentrations, as these compounds are reasonably to highly soluble in water. If complete removal of the alkali metal ions is not required, in some embodiments the produced AADA or its salt may be better soluble in water and can be reacted in higher concentrations.

When almost all the alkali metal ions should be removed from the aqueous solution of AADA alkali metal salt, the concentration must be adjusted beforehand in order to avoid the precipitation of crystals of AADA during the dialysis, depending on the solubility of the pertinent AADA.

The aqueous solution A may be an aqueous acidic solution, an aqueous alkaline solution or a neutral aqueous solution, like water (tap water suffices). In a preferred embodiment the aqueous solution is a neutral or (slightly) alkaline solution. More preferred is the use of a neutral or slightly alkaline aqueous solution, most preferably having a pH between 7 and 8.

The aqueous solution A is preferably used in several installments and is replaced during the electrodialysis, because the use of the whole of the calculated required amount will cause deterioration of the current efficiency. Such an installment use can reduce the concentration of alkali metal ions in the aqueous solution of AADA alkali metal salt with efficiency. The aqueous solution may be circulated and recycled.

If the aqueous solution contains an acid, base or salt, the concentration of the aqueous acid, alkaline or salt solution in one embodiment should fall in the range from 1 to 40 wt %. The concentration more preferably is 5 wt % or more, and typically preferably 8 wt % or more, and more preferably is 20 wt % or less, and typically preferably 15 wt % or less. If the concentration of the aqueous acid solution exceeds 40 wt %, excess amounts of sulfuric ions and other bases may migrate into the aqueous solution of AADA salt, and crystals of sodium sulfate or another alkali metal salt may be precipitated to plug the membrane at low temperatures of the solution. On the other hand, if it is less than 1 wt %, the proportion of the circulated aqueous acid solution must be increased, resulting in an increased volume of a reservoir.

As an electrode solution E to be circulated in electrode cells, an alkaline, acidic or neutral solution may be used, as long as it sufficiently conducts the electric current needed. In one embodiment the solution may be a solution of an acid, base or salt in a concentration of between 0.5 and 10 wt %, preferably between 1 and 5 wt %, most preferably 1 to 2 wt %. If an acidic solution is used, an acid identical to the one used for the dialysis is preferably employed. If the concentration of the electrode solution is too high, electrode plates may be corroded faster. On the other hand, if the concentration is too low, the electric current will hardly flow.

The applied electric power in the electrodialysis can be controlled either by a constant voltage method or a constant current method. At increased current density, the required treatment time decreases. However, increased current density requires increased voltage and therefore the electric power input increases. This results in a temperature increase in the solution generated by the ohmic losses in the electrodialysis unit. Accordingly, the upper limit of both potential and current is preferably controlled so as to maintain the temperature of the solution within such a range as will not cause deterioration of the membranes.

The electrodialysis operation is generally performed in a batch system, and the aqueous solution of AADA alkali metal salt is exchanged after completion of each dialysis operation. However, the aqueous solution A does not need to be exchanged at the same time and can be used until in the course of a next batch operation and then replaced with a new portion of the aqueous solution. By this operation, the concentration of alkali metal ions in the aqueous solution of AADA alkali metal salt can be reduced with efficiency. Naturally, the electrodialysis can be performed continuously by connecting a multiplicity of dialyzers to constitute a multistage dialyzer.

In the batch treatment, the completion of the electrodialysis operation should be determined by whether the concentration or pH value of the aqueous solution of AADA alkali metal salt reaches a predetermined value. When the electrodialysis is performed in order to form an AADA aqueous solution from which alkali metal ions are removed, the electrodialysis operation should preferably be completed at the time when the concentration of alkali metal ions reaches the lower permissible limit or sooner. This is because excessive electrodialysis for the purpose of complete removal of the alkali metal ions will cause the current efficiency to deteriorate and increase the amount of acid ions and bases to migrate and contaminate the AADA solution

EXAMPLES

Example 1

Determination of a number of properties of some partially acidified AADAs compared to the full metal salts of these AADAs, such as viscosity, conductivity, and corrosiveness in water Commercial Dissolvine® GL-38, Dissolvine® H-40 ex Akzo Nobel Chemicals, and Trilon® M ex BASF were used as reference GLDA-Na4, HEDTA-Na3, and MGDA-Na3, respectively. The partially acidified chelates (40% in water) were prepared by addition of the corresponding chelate acid (in water) to the commercial product until the highest pH was obtained at which less than 0.1 wt % fully neutralized chelate is present. GLDA-H4 was prepared by electrodialysis and MGDA-Na$_{x<3}$H$_{3-x}$ was made from Trilon® M by ion exchange. The desired pH was derived from the species distribution graphs that are based on the protonation constants. The resulting chelate solutions all have a chelate content (Fe-TSV) between 38.3 and 43 wt % of the salt actually present.

The corrosiveness against aluminium was determined using unspecified aluminium plates. The aluminium plates of 6×3×0.2 cm, supplied by the technical service, were cleaned with ethanol cleaner and dried and the weight of the plates was measured. Subsequently, the plates were completely submerged in the commercial or partially acidified chelate solution and kept at RT. In time, the plates were removed from the solutions, rinsed, dried by technical air, and weighted. The corrosiveness was expressed as the weight loss after a certain period of time. Furthermore, the aluminium plates and the chelate solution were visually inspected to evaluate the corrosion process.

The pH of the c. 40 wt % chelate solution as such was determined by a glass electrode.

The conductivity was measured with a Knick Konductometer 703.

The viscosity was determined with a Brookfield DV-II+ pro viscometer, using a S-18 spindle. The temperature was maintained with a cryostat.

The physical properties are listed in Table 1.

TABLE 1 the physical properties of (partially acidified) GLDA, HEDTA, and MGDA

|  | GLDA-Na4 | GLDA-Na3H | HEDTA-Na3 | HEDTA-Na2H | MGDA-Na3 | MGDA-Na2H |
|---|---|---|---|---|---|---|
| Source | GL-38 | GL-38 + 38 wt % GLDA-H4 in water | H-40 | H-40 + 40 wt % HZ in water | Trilon M | Trilon M |
| Fe-TSV (wt %) | 38.30% | 38.86 wt % | 42.97% | 41.3% | 40.32% | 39.92% |
|  | GLDA-Na4 | GLDA-Na3H | HEDTA-Na3 | HEDTA-Na2H | MGDA-Na3 | MGDA-Na2H |
| Fe-TSV as (mol/kg) | 1.09 | 1.18 | 1.25 | 1.28 | 1.49 | 1.60 |
| Conductivity (mS/cm) at 20° C. | 20.9 | 29.89 | 20.29 | 24.1 | 25.8 | 37.3 |
| pH | 13.5 | 7.2 | 13.4 | 7.4 | 13.5 | 7.4 |
| Viscosity at 20° C. (Mpas) | 51.5 | 30.1 | 31 | 14.1 | 26 | 11.0 |
| Viscosity at 40° C. (Mpas) | 21.4 | 12.1 | 14.7 | 7.1 | 11.0 | 6.3 |
| Corrosiveness Aluminium (% weigth loss after 70 hr) | 7 | <0.1 | 7 | <0.1 | 6 | <0.1 |

Conclusions

Partially acidified c. 40 wt % sodium GLDA, HEDTA, and MGDA are less corrosive for aluminium, more conductive, and less viscous than their fully neutralized counterparts Example 2

Electrodialytical Acidification of GLDA-Na$_2$H$_2$ (pH≈7.2)

FIG. 1 is a schematic diagram illustrating an electrodialyzer (Eurodia Industrie SA: EUR2c-7 Bip) used in the present example. An aqueous basic solution (sodium hydroxide solution) is circulated with a circulation pump (not shown) from a reservoir (not shown) through an intermembranous space indicated as "aqueous base solution A" in the figure and returned to the reservoir. The concentration of sodium hydroxide is 5 wt %. An electrode solution E at the start of the process containing about 5 wt % sodium hydroxide is fed with a circulation pump (not shown) from a reservoir (not shown) to both electrode cells and circulated to the reservoir. A cell indicated as "sample S" in the figure is a cell into which a sodium AADA solution (optionally partly acidified) flows, and this sodium AADA solution is circulated with a circulation pump (not shown) from a reservoir (not shown) through an intermembranous space of the electrodialyzer to the reservoir.

Hydrogen ion permselective membranes (Tokuyama Corp.: Neosepta BP1E, indicated as "H" in the figure), cation-permeable membranes (Tokuyama Corp.: Neosepta CMB, indicated as "C" in the figure), and a thick-film cation-permeable membrane (Tokuyama Corp.: Neosepta C66-10F, indicated as "T") were placed in the arrangement shown in FIG. 1. The number of effective sets for dialysis was seven and the effective area of each membrane was 200 cm$^2$.

The electrodialysis was performed in the set-up of FIG. 1 in the following manner: A total of 1.8 kg of a solution of tetrasodium glutamic acid-N,N-diacetate (tetrasodium glutamic acid-N,N-diacetate: 40.2%, pH 7.2) made by mixing an aqueous solution of tetrasodium glutamic acid-N,N-diacetate (tetrasodium glutamic acid-N,N-diacetate: 50%, pH 13.5) with concentrated hydrochloric acid solution (37 wt % HCl) and adjusting the concentration by means of evaporation, initially 1.5 kg (5%) of a sodium hydroxide solution, and 3 kg of an electrode solution (5% sodium hydroxide) were placed in individual reservoirs, and electrodialysis was performed while circulating each solution with a pump. A constant current of 15 amperes was fed for 80 minutes at a voltage between 15.7 and 16.7 volts. A total amount of 75 Wh of DC electric energy is consumed per mole of glutamic acid-N,N-diacetate. The obtained solution of glutamic acid-N,N-diacetic acid was 1.6 kg (glutamic acid-N,N-diacetic acid: 44.7%, pH 1.9).

Comparative Example 3

Acidification of GLDA-Na4 (pH≈13.5)

The electrodialysis was performed in the following manner: A total of 1.7 kg of a solution of tetrasodium glutamic acid-N,N-diacetate (tetrasodium glutamic acid-N,N-diacetate: 37.0%, pH 13.5), initially 1.5 kg (5 wt %) of a sodium hydroxide solution, and 3 kg of an electrode solution (5 wt % sodium hydroxide) were placed in individual reservoirs, and electrodialysis was performed while circulating each solution with a pump. A constant current of 15 amperes was fed for 120 minutes at a voltage between 16 and 20 volts. A total amount of 111 Wh of DC electric energy is consumed per mole of glutamic acid-N,N-diacetate. The obtained solution of glutamic acid-N,N-diacetic acid was 1.3 kg (glutamic acid-N,N-diacetic acid: 47.5%, pH 2.0).

Conclusions of Example 2 and Comparative Example 3

The energy consumption for producing GLDA at pH=2 is 32% less when a HCl pre-acidified GLDA-Na$_4$ solution is used (Ex. 2) compared to starting with a strongly basic (pH=13.7) GLDA-Na$_4$ product (Comp. Ex. 3).

The required BPM unit for producing GLDA at pH=2 is 36% smaller when a HCl pre-acidified GLDA-Na$_4$ solution (Ex. 2) is used compared to starting with a strongly basic (pH=13.7) GLDA-Na$_4$ product (Comp. Ex. 3).

Increased concentrations can be treated in a BPM unit when a HCl pre-acidified GLDA-Na$_4$ solution (pH=7.2, Ex. 2) is acidified to pH=2 compared to doing the same but starting with a strongly basic (pH=13.7, Comp. Ex. 3) GLDA-Na$_4$ solution.

Examples 4 to 6 and Comparative Examples 7 and 8

Acidifying an aqueous solution of an AADA-salt with 100% BPM electrodialysis only (Comparative Example 7) was compared with combined acidifying with chemicals and BPM electrodialysis (75, 50, and 25% BPM, Examples 4 to 6, respectively), and with chemical acidification only (Comparative Example 8).

As the AADA-salt a 40 wt % GLDA-Na4 aqueous solution was used and the acid for the chemical acidification was 37% HCl in water. The BPM was performed according to the method used in Example 2, where the amount of HCl used determines the required duration of the electrodialysis step (the less HCl, the longer the electrodialysis step).

The results are given in FIG. 2 below.

The results are given in FIG. 1 which shows a comparison of water balance in different acidification processes.

In FIG. 1 it can be seen that after fully acidifying with BPM, an extremely concentrated fully protonated AADA composition is acquired as a consequence of an electro-osmotic effect (by which water is transported with the sodium ions to another cell).

After fully chemically acidifying GLDA the end product GLDA-H4 is clearly much more dilute than the starting product GLDA-Na4. This water can of course be removed by, e.g., an evaporation step, but this will inherently lead to further energy consumption and also further increase the already considerable salt concentration in the end product (which amounts to about 12 wt % already after the acidification). The AADA can easily crystallize during the water removal, even more so in the presence of a high salt concentration, which will lead to further complications in the processing of the AADA end product.

However, it is demonstrated that when using a chemical acidification until at least one group is fully protonated and subsequently further acidifying by means of a BPM electrodialysis step, an AADA-acid concentration results that is close to the concentration of the starting material, the AADA-salt. The desired concentration can also be easily fine-tuned by switching from the chemical acidification to the electrodialytical BPM acidification at the right moment.

The invention claimed is:
1. A process for the production of an amino acid having at least one secondary or tertiary amino group and three or more carboxyl groups or its salt with less than an equivalent of alkaline metal based on the number of carboxyl groups, said process comprising reducing alkali metal ions from an aqueous solution of an alkali metal salt of an amino acid having at least one secondary or tertiary amino group and three or more carboxyl groups and acidifying an amino carboxylate starting material by first performing a chemical acidification step using an organic or inorganic acid to get a compound in which at least one of the groups is protonated, and in a subsequent step further acidifying the amino carboxylate starting material and reducing alkali metal ions from an aqueous solution of the partially acidified alkali metal salt of the amino acid having at least one secondary or tertiary amino group and three or more carboxyl groups by electrodialysis, wherein the electrodialysis is performed using a hydrogen ion permselective membrane on the anode side and a cation-permeable membrane on the cathode side.

2. The production process according to claim 1 wherein said alkali metal salt of an amino acid is an alkali metal salt of an amino acid-N,N-diacetic acid.

3. The production process according to claim 2 wherein said alkali metal salt of an amino acid-N,N-diacetic acid is a salt represented by the following formula (1):

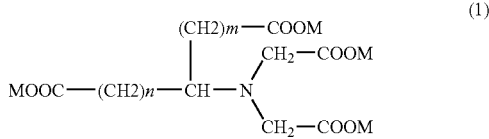

or formula (2)

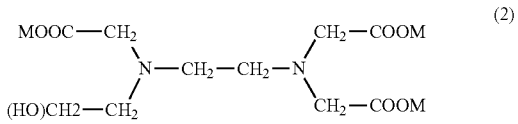

wherein M represents an alkali metal, m represents 0 or an integer of from 1 to 2, and n represents 0 or an integer of from 1 to 3.

4. The production process according to claim 3 wherein said alkali metal salt of an amino acid-N,N-diacetic acid is an alkali metal salt of N-hydroxyethyl ethylenediamine N,N',N'-triacetic acid, methylglycine N,N-diacetic acid, or glutamic acid-N,N-diacetic acid.

5. The process according to claim 4 wherein the chemical acidification is performed using the organic acid or inorganic acid selected from the group consisting of formic acid, acetic acid, glycolic acid, oxalic acid, citric acid, propionic acid, hydrochloric acid, hydrobromic acid, sulfuric acid, phosphoric acid, nitric acid, and aqueous solutions thereof.

6. The process according to claim 4 wherein the chemical acidification step is performed using the amino acid or its salt with less than an equivalent of alkaline metal produced by electrodialysis.

7. The process according to claim 3 wherein the chemical acidification is performed using the organic acid or inorganic acid selected from the group consisting of formic acid, acetic acid, glycolic acid, oxalic acid, citric acid, propionic acid, hydrochloric acid, hydrobromic acid, sulfuric acid, phosphoric acid, nitric acid, and aqueous solutions thereof.

8. The process according to claim 3 wherein the chemical acidification step is performed using the amino acid or its salt with less than an equivalent of alkaline metal produced by electrodialysis.

9. The production process according to claim 2 wherein said alkali metal salt of an amino acid-N,N-diacetic acid is an alkali metal salt of N-hydroxyethyl ethylenediamine N,N',N'-triacetic acid, methylglycine N,N-diacetic acid, or glutamic acid-N,N-diacetic acid.

10. The process according to claim 9 wherein the chemical acidification is performed using the organic acid or inorganic acid selected from the group consisting of formic acid, acetic acid, glycolic acid, oxalic acid, citric acid, propionic acid, hydrochloric acid, hydrobromic acid, sulfuric acid, phosphoric acid, nitric acid, and aqueous solutions thereof.

11. The process according to claim 9 wherein the chemical acidification step is performed using the amino acid or its salt with less than an equivalent of alkaline metal produced by electrodialysis.

12. The process according to claim 2 wherein the chemical acidification is performed using the organic acid or inorganic acid selected from the group consisting of formic acid, acetic acid, glycolic acid, oxalic acid, citric acid, propionic acid, hydrochloric acid, hydrobromic acid, sulfuric acid, phosphoric acid, nitric acid, and aqueous solutions thereof.

13. The process according to claim 2 wherein the chemical acidification step is performed using the amino acid or its salt with less than an equivalent of alkaline metal produced by electrodialysis.

14. The process according to claim 1 wherein the chemical acidification is performed using the organic acid or inorganic acid selected from the group consisting of formic acid, acetic acid, glycolic acid, oxalic acid, citric acid, propionic acid, hydrochloric acid, hydrobromic acid, sulfuric acid, phosphoric acid, nitric acid, and aqueous solutions thereof.

15. The process according to claim 1 wherein the chemical acidification step is performed using the amino acid or its salt with less than an equivalent of alkaline metal produced by electrodialysis.

* * * * *